United States Patent [19]
Call

[11] Patent Number: 5,433,707
[45] Date of Patent: Jul. 18, 1995

[54] SYRINGE FOR BALLOON CATHETERIZATION

[75] Inventor: Evan Call, Bountiful, Utah

[73] Assignee: Surgical Technologies, Inc., Salt Lake City, Utah

[21] Appl. No.: 208,970

[22] Filed: Mar. 9, 1994

Related U.S. Application Data

[63] Continuation-in-part of Ser. No. 30,567, Mar. 12, 1993, Pat. No. 5,318,534.

[51] Int. Cl.$^6$ .......................................... A61M 29/00
[52] U.S. Cl. ........................................ 604/97; 604/99
[58] Field of Search ................ 604/97, 98, 99, 100, 604/211, 214, 188, 146

[56] References Cited

U.S. PATENT DOCUMENTS

| | | | |
|---|---|---|---|
| 4,370,982 | 2/1983 | Reilly | 604/99 |
| 4,583,974 | 4/1986 | Kokernak | 604/211 |
| 4,651,738 | 3/1987 | Demer et al. | 606/102 |
| 4,710,179 | 12/1987 | Haber et al. | 604/211 |
| 4,723,938 | 2/1988 | Goodin et al. | 604/99 |
| 4,740,203 | 4/1988 | Hoskins et al. | 604/97 |
| 4,758,223 | 7/1988 | Rydell | 604/98 |
| 4,810,249 | 3/1989 | Haber et al. | 604/211 |
| 4,832,692 | 5/1989 | Box et al. | 604/211 |
| 4,919,121 | 4/1990 | Rydell et al. | 604/99 |
| 4,940,459 | 7/1990 | Noce | 604/99 |
| 5,019,041 | 5/1991 | Robinson et al. | 604/211 |
| 5,047,015 | 9/1991 | Foote et al. | 604/98 |
| 5,084,060 | 1/1992 | Freund et al. | 604/100 |
| 5,137,514 | 8/1992 | Ryan | 604/99 |
| 5,147,300 | 9/1992 | Robinson et al. | 604/211 |
| 5,318,534 | 11/1994 | Williams et al. | 604/97 |

Primary Examiner—C. Fred Rosenbaum
Assistant Examiner—N. Kent Gring
Attorney, Agent, or Firm—Trask, Britt & Rossa

[57] ABSTRACT

A unique syringe useful in the inflation and rapid deflation of a balloon used in balloon catheterization (transluminal angioplasty) procedures is disclosed. The syringe has a uniquely actuated thread engaging block which is engaged and disengaged by a rotary cam member interacting with the thread-engaging block. The thread engaging block engages a threaded piston rod which is attached to the piston within the barrel of a balloon catheter syringe. A rotary cam member engages the block so as to exert a positive force on the block, either moving the block into a thread engaging position or moving into a thread disengaging position. The unique syringe may also contain a plunger end face which is structured so that a portion of the piston face is separately actuatable in order to introduce a minor increase or decrease in pressure while the main piston member remains in a stationary position.

12 Claims, 10 Drawing Sheets

SYRINGE FOR BALLOON CATHETERIZATION

RELATED APPLICATION

This application is a continuation-in-part of application Ser. No. 08/030,567 now U.S. Pat. No. 5,318,534 filed Mar. 12, 1993, having a common inventor and common assignee.

BACKGROUND OF THE INVENTION

1. Field of the Invention

The instant invention relates to syringes for inflating a balloon in a balloon catheterization device and to the systems and methods associated with balloon catheterization (transluminal angioplasty procedures).

2. State of the Art

Numerous syringes for balloon catheterization are extant in the art. A representative sampling of such syringes are disclosed in the following patents: U.S. Pat. Nos. 5,047,015 to Foote et al.; 4,832,692 to Box et al.; 4,651,738 to Demer et al.; 4,940,459 to Noce et al.; 4,583,974 to Kokernak and 5,084,060 to Freund et al. An exhaustive list of additional patents exists in the references-cited portion of the Foote et al patent.

Devices disclosed in the above-identified patents are quite similar in structure, having a barrel and plunger or piston configured so that the piston may be screwed into the barrel in small increments to increase pressure on fluid within the barrel. Ultimately, the pressurized fluid flows into the balloon in a slow, controlled manner to inflate the balloon. Generally, all syringes disclosed in the above-identified patents have a quick release mechanism whereby the threaded engagement between the threaded piston rod and the internal threads within the syringe body are quickly disconnected, allowing the piston rod and piston to slide freely within the device and be quickly retracted to reduce rapidly fluid pressure within the balloon.

Various techniques and means are employed to bring about the disengagement between the threaded portions of the piston rod and the syringe housing, In the Foote et al, patent the threads on the piston rod are permitted to retract when a trigger mechanism is pulled to cause the piston rod threads to slide along an inclined plane to remove them from contact with the threads of the syringe body, In Box et al, a lever on top of the syringe is pushed towards the syringe by the palm of the hand to press against a threaded member to push that threaded member away from contact with the threads of the piston rod.

Techniques have recently been utilized by operators of balloon catheter syringes whereby the plunger rod is rapidly rotated back and forth to use a pressure pulsation where the balloon is in contact with a plaque construction,

SUMMARY OF THE INVENTION

The invention relates, in one aspect, to an improved balloon catheterization syringe having a pair of concentric pistons which form the plunger of the syringe. An outer piston is moveable within the syringe barrel in a conventional manner. The outer piston contains an end cap, preferably of a unitary structure, which is flexible and preferably forms a peripheral seal within the barrel. The second piston is contained within an axial bore of the outer piston so that the secondary piston may be reciprocated to contact the inner surface of the flexible end cap to distend the face of the end cap, or to allow it to collapse if it is under fluid pressure; thus, by repeated distending or collapsing a pulsating pressure can be created within the syringe barrel.

The instant invention involves a syringe for balloon catheterization in which the threads (splines) contained within the body of the syringe on a splined block and the threads on the piston rod connected to, and an integral part of the piston, are engaged and disengaged manually by manual positive action, or in alternative embodiments, through the use of a spring. Further, the syringe is constructed so that it may be held in one hand, for example, the left hand and the threaded engagement means, preferably a threaded block, operated by one thumb upon a handle connected to a screw element (rotary cam) which retracts and engages said threaded block which is structured to engage the threads of the piston rod. Thus, the syringe may be held in the left hand and, with the right hand, turn the piston rod which screws the piston into the body of the syringe thereby advancing the plunger within the barrel chamber to create fluid pressure within the balloon attached to plastic tubing connected to the discharge end of the barrel.

In order to disengage the threaded piston rod, the thumb of the left hand, for example, may be placed upon the wing-like handle of the retraction/insertion member (rotary cam) whereby the handle is moved (rotated) from an engagement position to a disengagement position which rotates the rotary cam to retract the splined block. Both the retraction and engagement action of the splined block is controlled by a positive positioning action that is either a clockwise or a counterclockwise rotation of the rotary cam.

An advantage of one embodiment of the device of the instant invention is that the splined block may be retracted and left in a retracted position. There is no spring bias upon the block which would force it back into an engagement position as in other devices and in other embodiments described herein. Furthermore, in manually retracting the splined block there is no spring bias which must be overcome by force applied by the operator to cause such disengagement. The only force that must be overcome is the force which exists on the splined block because of pressure reaction of the pressurized fluid upon the piston.

The device of the instant invention comprises a syringe body which supports a cylindrical barrel at its distal end. The barrel, at its proximal end, has a wide mouth opening which permits the insertion of a piston member (plunger) within the barrel. The plunger fits tightly within the barrel and generally is sealed to the barrel by o-rings or by a rubbery, unitary, membrane-like end cap (flexible face) on the end of the plunger whereby the rubbery cap has a diameter slightly greater than the piston so that it seals the piston to the interior wall of the barrel. A threaded piston rod, which preferably is of a large diameter equal to or only slightly smaller than the diameter of the piston, is attached to or is integral with the proximal end of the piston. The piston rod is threaded and extends outward of the proximal end of the syringe body.

A splined block is contained within the syringe body and is oriented substantially perpendicularly to the longitudinal axis of the piston rod. The splined block is attached to an insertion/retraction member (rotary cam) which is a screw-like member which fits within the splined block and is also oriented substantially perpendicularly to the longitudinal axis of the piston rod.

The retraction/insertion member protrudes through the top wall of the syringe body (it is preferably the top wall although it could be either side wall or the bottom wall) with a wing-like handle attached radially to the insertion/retraction member (rotary cam) so that it is substantially parallel to the longitudinal axis of the piston rod and is in a position relative to the syringe body so that the wing-like handle may be manipulated easily with the thumb of the left hand while the left hand is gripping the syringe body from underneath, that is, the palm of the left hand would be in contact with the underside of the syringe body. Another particularly good feature of this invention is that it may be readily operated by either right or left handed people with or without a minor change in the orientation of the winged-handle.

Further description of the invention may be facilitated by reference to the following drawings.

DETAILED DESCRIPTION OF THE INVENTION

Figure 1:
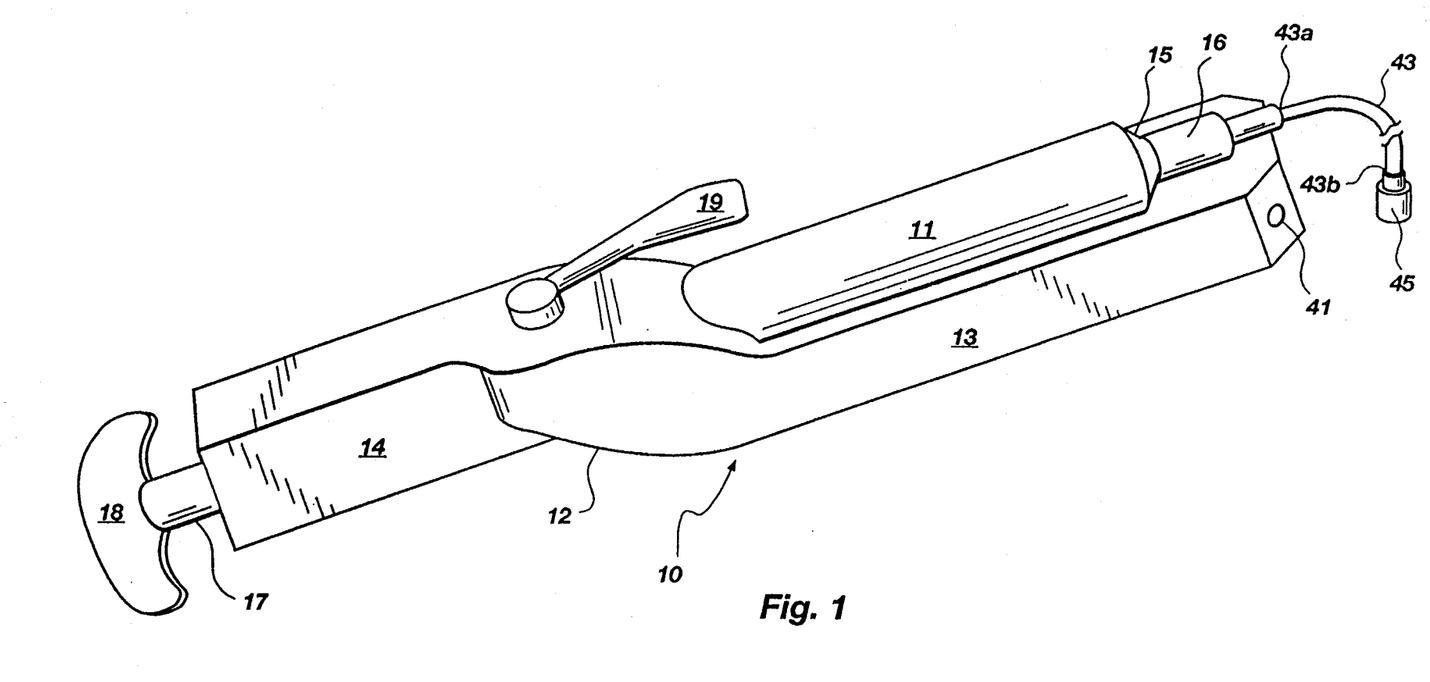
FIG. 1 is a perspective view of the balloon catheter syringe of the instant invention.

A preferred embodiment of the invention is illustrated in FIG. 1, which is a perspective view of a balloon catheter syringe 10 having a cylindrical barrel 11 supported by an elongated syringe body 12 which has a barrel supporting portion 13 and a hand-grip portion 14. The discharge end of the barrel has a cone-shaped end 15 which is integral with a nozzle 16. The nozzle may connect to a flexible tubing which forms part of the tubing that is inserted into a vein or artery. In a preferred construction, a flexible tubing member 43 is connected to the nozzle 16 at the first end 43a and is fitted on its opposing end 43b with a Luer connector 45. The luer connector in turn may be fitted with a conventional catheter (not shown). At the proximal end of the syringe body, a piston rod 17 projects towards the person using the device and is capped with a handle 18.

On the top surface of the syringe body is a wing-like handle 19, which can be rotated from a first position which is an engagement position which causes engagement between the threads of the piston rod, and the splined block, said handle 19 being rotatable to a second position which is a disengagement position for the splined block.

Figure 2:
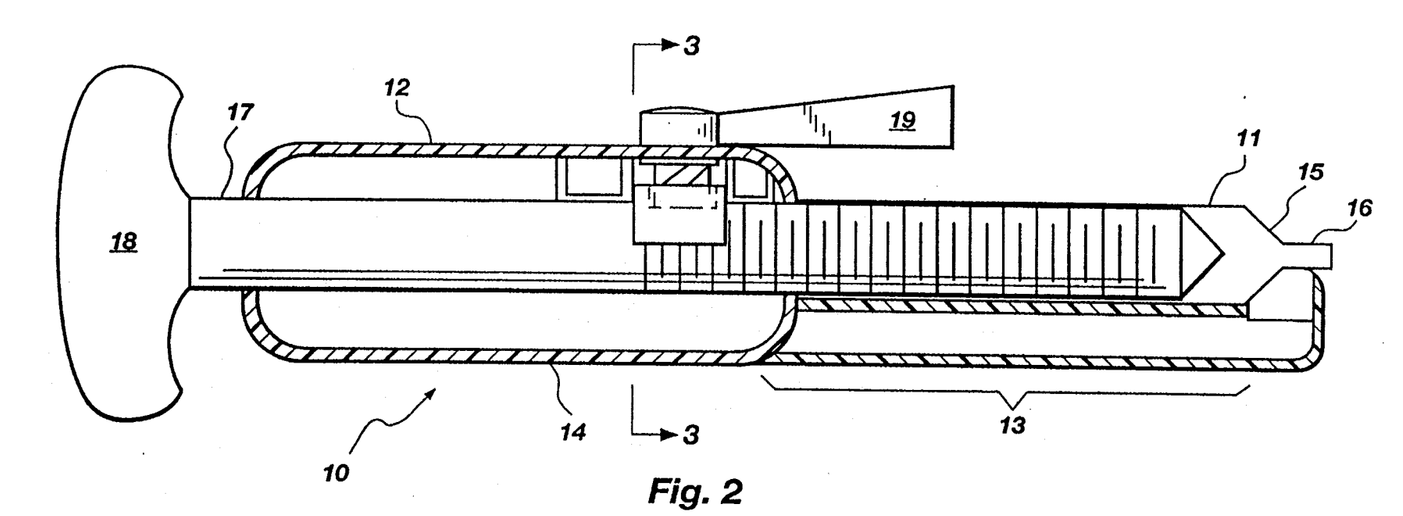
FIG. 2 is an elevational, partial, sectional view of the syringe of FIG. 1 along section lines 2—2.

FIG. 2 is an elevational partial sectional view of the balloon catheter syringe illustrating the interaction of the splined moveable block and the piston rod/plunger. As illustrated to be seen that the piston rod is the same diameter as the plunger and, as will be noted in other embodiments, the piston rod may be hollow to accommodate another interior rod. The piston portion of the piston rod plunger unit fits within the cylindrical barrel of the unit. The barrel is supported by the syringe body and has a proximal open end with a supporting flange around its said open end, it being the same diameter as the interior of the barrel to accommodate the entrance of the piston into the barrel.

Figure 3:
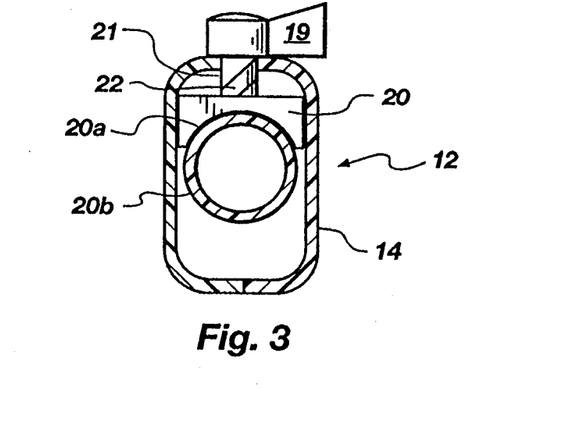
FIG. 3 is a sectional view of the syringe of FIG. 1 along section lines 3—3.
Figure 4:
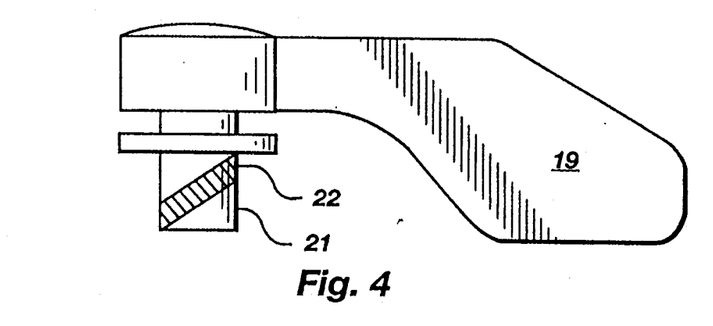
FIG. 4 is an elevational view of the actuator mechanism of the syringe of FIG. 1.

FIGS. 3 and 4 illustrate the quick release mechanism of the instant invention wherein a winged handle 19 is attached to a cylindrical pin-like element 21 which has a cam race 22 within it, wherein the cam race 22 interacts with a protrusion (not shown) within the threaded block 20 so that rotation of the pin-like member causes the splined block 20 to move upward or downward depending upon the rotation of the wing-like handle 19 attached to the pin-like cam member 21.

Figure 15:
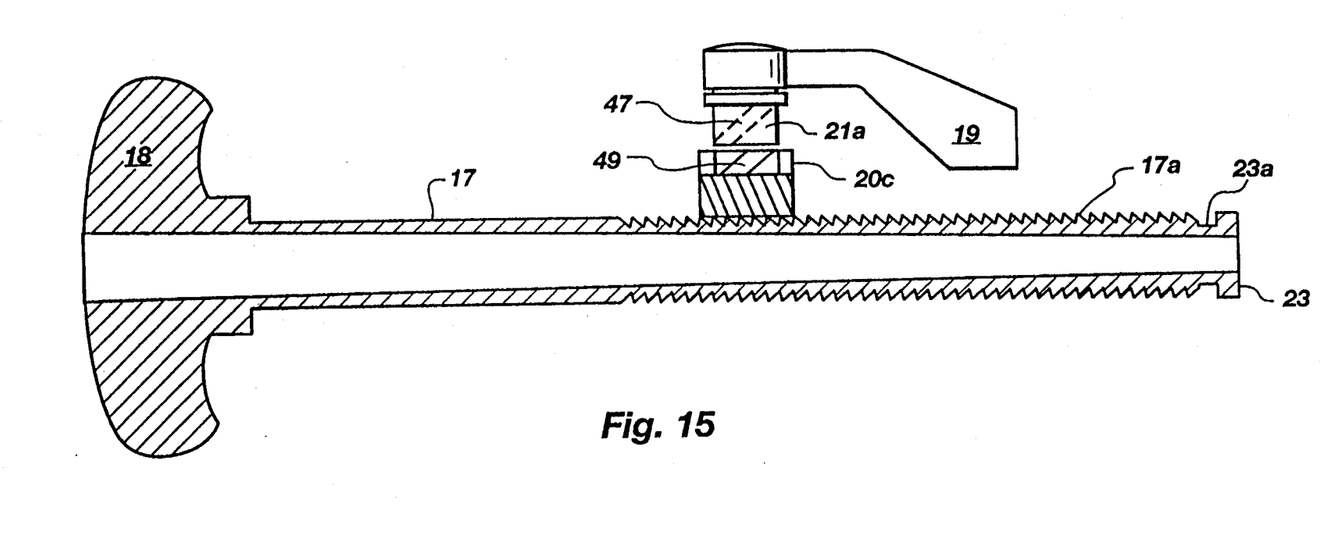
FIG. 15 is a cross-sectional side view of an alternative construction of a threaded piston rod of the invention.

In an alternative embodiment, illustrated in FIG. 15, a raised spiral cam surface 47 may be defined on the pin-like member 21a to interact with a spiral race 49 defined in the inner surface wall of the block 20c which receives the pin-like member 21a.

Preferably, the pitch of the cam threads is about two threads per inch, which causes about a one-eighth inch displacement of the block for each 90° of rotation of the pin.

The threaded block 20 has a partial-cylindrical surface 20a which is threaded to interact with the threads on the threaded piston rod 17. The threads on surface 20a are the only threads associated with the internal base 20b of the syringe body. Thus, when the threaded block 20 is in an upward position, the threads on the piston rod 17 are disengaged, allowing the piston rod to move freely to the rear when fluid pressure within the barrel pushes on the piston. Surface 20a is preferably less than a semi-cylindrical surface so that less upward movement is required to cause disengagement between the threaded piston rod and the threads on surface 20a.

The term "splines" has also been used herein to describe the threads on surface 20a.

The pin-like member 21 may have conventional threads on its surface so that it "screws" into threaded block 20 to move it upwards. Also, the pin-like member 21 may be secured to the block 20 in a rotatable manner with its threads interacting with threads in the top surface of the syringe to cause the pin-like member to rise when rotated in one direction and to carry said block 20 with it, thereby raising the block to cause it to disengage from threads on the piston rod. Rotation of the pin-like member in the other direction would cause the block to lower and to engage the threads of the piston rod.

Figure 5:
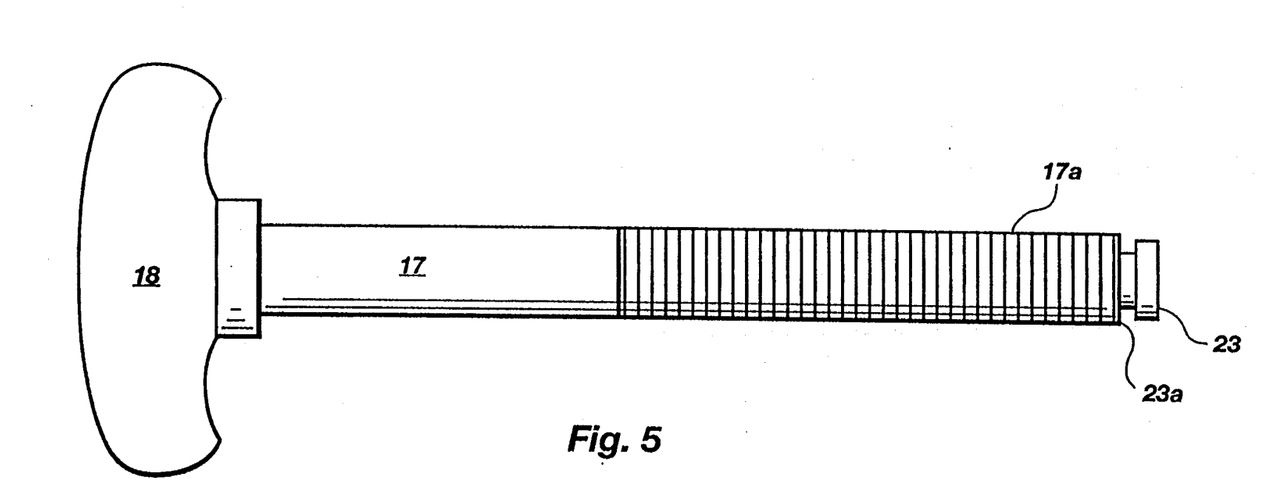
FIG. 5 is an elevational view of the piston rod of the syringe of FIG. 1.

The piston element of the invention is illustrated in more detail in FIG. 5 wherein a disc-like element 23 is attached to the distal end, that is, the pressure end, of the piston 17a. The smaller diameter disc 23 enables a plunger-tip (See FIG. 6) to be secured to the end of the plunger. The disc 23 is preferably integral with the piston and spaced slightly apart from the piston and leg groove 23a. The length of the piston rod is about 10 to 15 times the diameter of the piston. The piston rod handle 18, attached to the proximal end of the plunger, may be any general shape. It can be a knob although a flat, handle-like member is generally preferred.

Figure 6:
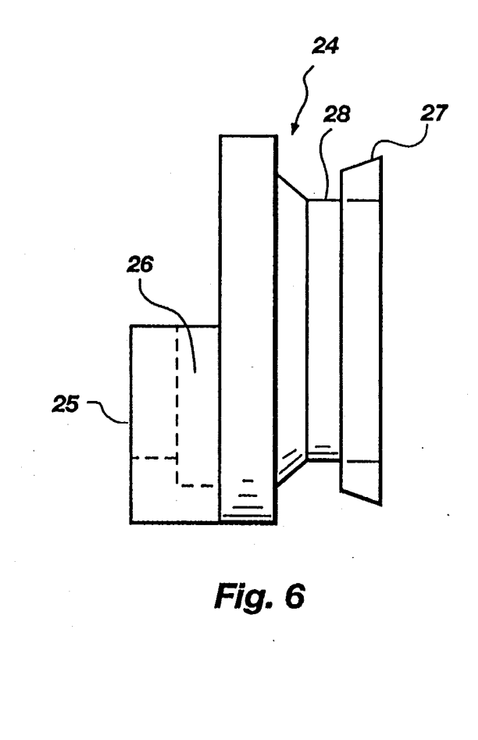
FIG. 6 is a side, elevational view of a plunger tip which interacts with the piston, i.e. plunger, end of the piston rod of FIG. 5.
Figure 7:
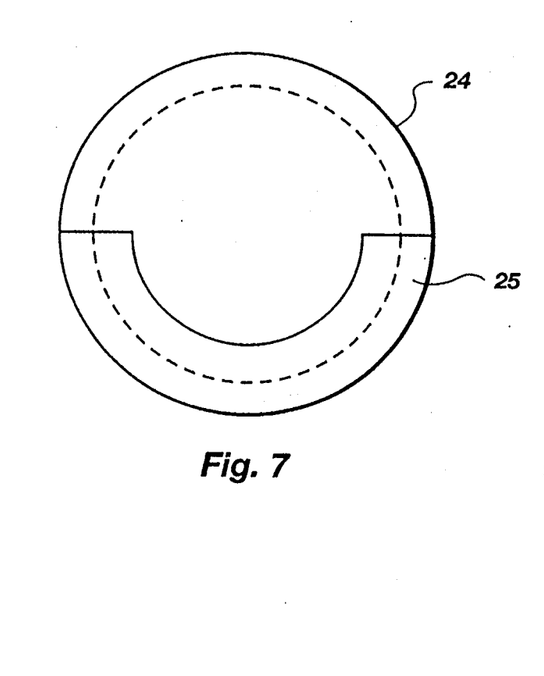
FIG. 7 is an elevational, rear view of the plunger tip of FIG. 5.

The plunger tip 24 is illustrated in FIGS. 6 and 7 and is designed with a semi-circular cup 25 to fit partially over the disk-like member 23 on the tip of the piston 17a. However, in the instant embodiment it is a separate element whereby the semi-circular cup 25 has a semi-circular cavity 26 which mates with the disk 23 on the tip of the plunger to hold the plunger tip 24 in place when the elements are within the barrel of the syringe. The plunger tip 24 permits the piston 17a to rotate without causing the tip 24 to rotate. The plunger tip 24 further has the larger, disk-like element 27 and a groove 28 behind it to accommodate a flexible rubbery diaphragm (end cap) which is slightly larger than the plunger tip and is illustrated in FIG. 8.

Figure 8:
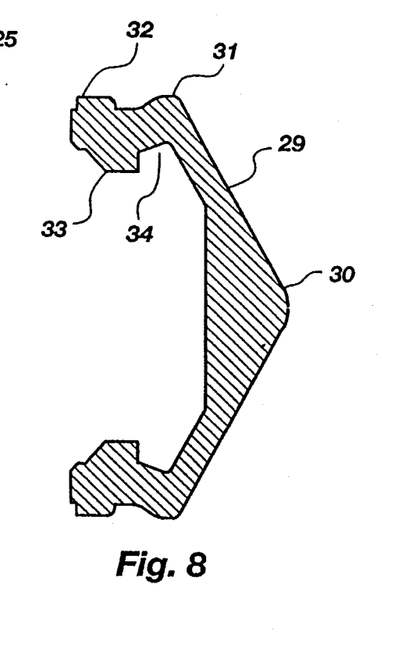
FIG. 8 is a side, elevational, sectional view of a circular, rubbery end cap which co-acts with the plunger tip of FIG. 7.

The diaphragm-like member 29 illustrated in FIG. 8 forms an end cap for the piston. It is a rubbery material and is of sufficient diameter that it seals the end of the plunger within the barrel so as the plunger moves forward into the liquid within the barrel, the liquid does not seep past the peripheral seal formed by the end cap. Thus, pressure can be exerted upon the liquid within the barrel. Other arrangements of constructing a plunger, of course, could be utilized. For example, the piston could have O-rings about the cylindrical circumference of the piston to form a seal. O-rings have been used in other syringe plungers to effectuate a seal between the piston and the internal barrel wall. Also, a threaded piston rod could be a separate element rotatably attached to the piston. Thus, rotation of the piston rod would advance the piston but the piston would not rotate. On such a structure the end cap could be attached directly to the piston without an intermediate plunger tip.

The end cap 29 has a front face 30 which is circular and continuous. Around its circumference it has a laterally protruding ring 31 which fits very tightly within the barrel of the device to form a pressure tight seal. A secondary seal is formed by seal ring 32 which is to the rear of seal ring 31. An internal collar 33, i.e. a circular internal ridge, is adapted to fit within groove 28 of the plunger tip (See FIGS. 6, 7, 11 and 12) to secure the end cap 29 to the plunger tip. A circular groove 34 in the end cap mates with the rim of disk 27 of the plunger tip 24 to hold the end cap 29 securely to the plunger tip.

Figure 9:
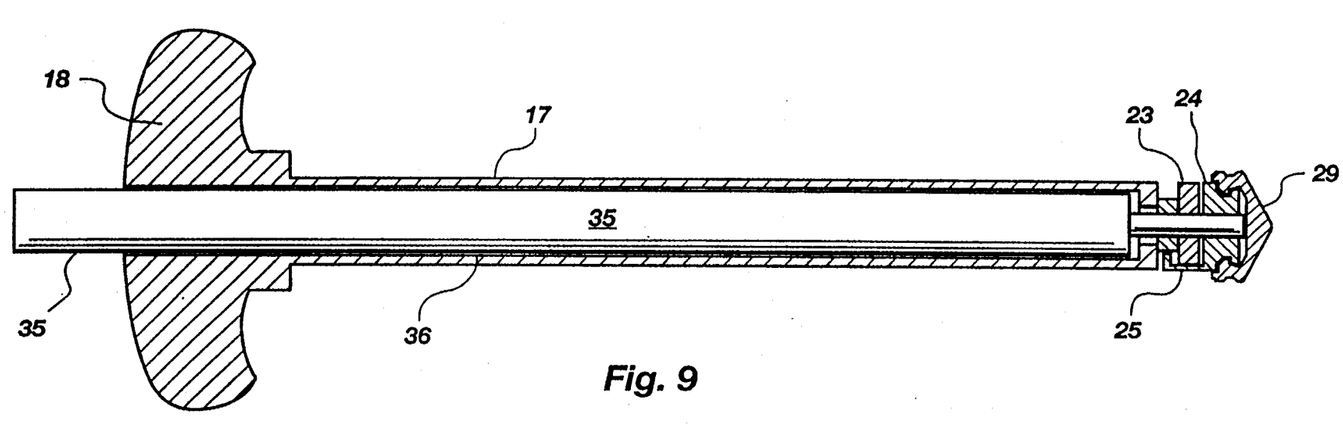
FIG. 9 is an elevational, sectional view of a syringe of the type illustrated in FIG. 1 with a dual piston comprising a main piston and a secondary piston.

FIG. 9 illustrates a syringe having a plunger assembly having a pair of concentric piston rods with a small piston rod 35 concentrically enclosed within the outer (main) piston rod 17. An elongated bore 36 completely through the center of the main piston rod/piston and plunger tip allows the small diameter, straight secondary piston rod to slide within the outer piston to contact the internal facial surface of rubbery end cap 29. The rear or proximal end of the secondary piston 35 protrudes from the rear of handle 18. An operator of the syringe can reciprocate secondary piston rod 35 longitudinally to distend the face of end cap 29 to increase the pressure in the barrel of the syringe and ultimately to increase the pressure within the balloon. Alternatively, the operator may retract the secondary piston rod 35 longitudinally to allow the end cap to collapse slightly to decrease pressure within the balloon.

Figure 11:
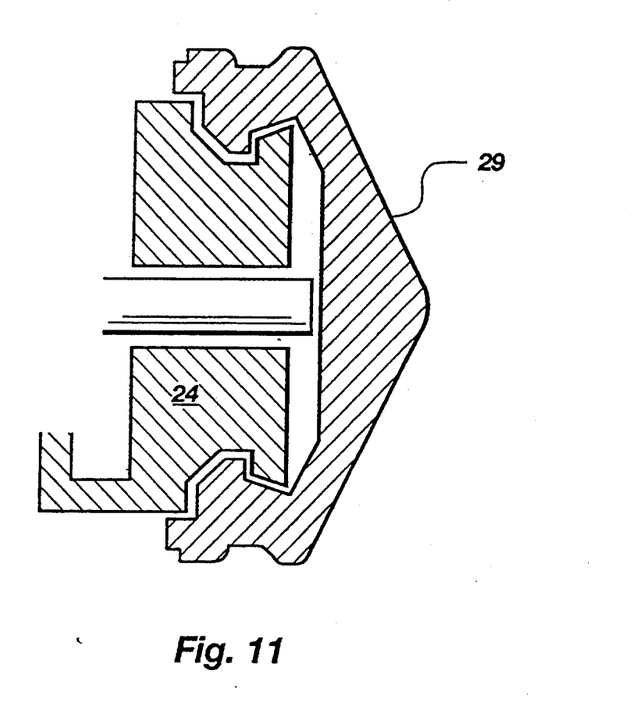
FIG. 11 is an enlarged view of the end cap portion of the syringe illustrated in FIG. 9 in a normal condition.
Figure 12:
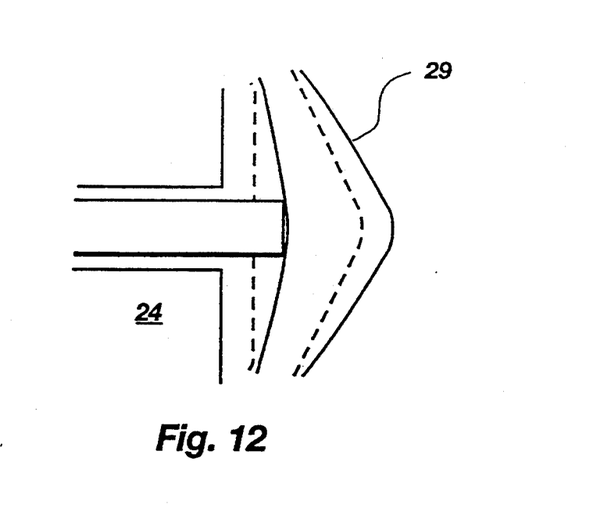
FIG. 12 is an enlarged view of the end cap portion of the syringe illustrated in FIG. 9 with the secondary plunger in a forward position, distending the rubbery end cap.

The normal position of the secondary piston rod is illustrated in FIG. 11. The distal end 35a of the piston rod presses through the plunger tip 24 to rest against the internal face of end cap 29. When the secondary piston rod 35 is pushed forward, it distends end cap 29 as illustrated in FIG. 12. The distal end 35a may, as illustrated, be slightly smaller in diameter than the diameter of secondary rod 35 so that it more easily passes through smaller openings in disk 23 and plunger tip 24.

Figure 10:
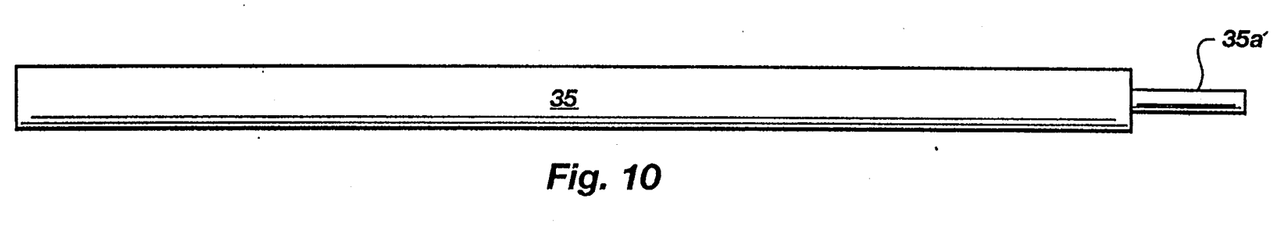
FIG. 10 is an elevational view of a secondary piston.

A particular advantage of the diaphragm-like end cap 29 is that an internal or secondary piston 35 can be concentrically fixed within the main piston rod 17. This is illustrated in FIG. 9. Also, FIG. 10 illustrates the secondary piston rod which is contained concentrically within the main piston rod 17.

The purpose of the secondary piston rod 35 is that when the main piston 17 has been threaded into the barrel a certain distance to achieve a certain desired pressure within the balloon of the balloon catheter, then by reciprocating the secondary piston, the diaphragm (end cap 29) is distended (see FIG. 12) into the liquid and a pulsating pressure may be applied to the balloon and thus effectuate a better compression of the plaque within a particular artery or vessel. (The dotted lines in FIG. 12 show the normal position for the face of end cap 29. The solid lines show the distend position.)

Some operating room technicians are currently achieving this pulsating pressure effect by rotating the main plunger back and forth rapidly to increase and decrease the pressure. However, such rotation of the main plunger may have certain risks in that it is perhaps easy to apply too much pressure and it can also be tiring to the wrist. In the instant invention, the device is constructed so that when one is holding the main piston, one can press on the secondary piston at its proximal end with a thumb or with the palm of the hand to slightly move the diaphragm at the distal end of the plunger to induce an increase in pressure of perhaps 10 to 40 percent. The maximum pressure increase can be designed into the unit by predetermining the diameter of the secondary piston and predetermining the distance which the secondary piston rod at its proximal end projects from the handle so as to control the amount of distortion of the diaphragm into the catheter fluid.

Figure 13:
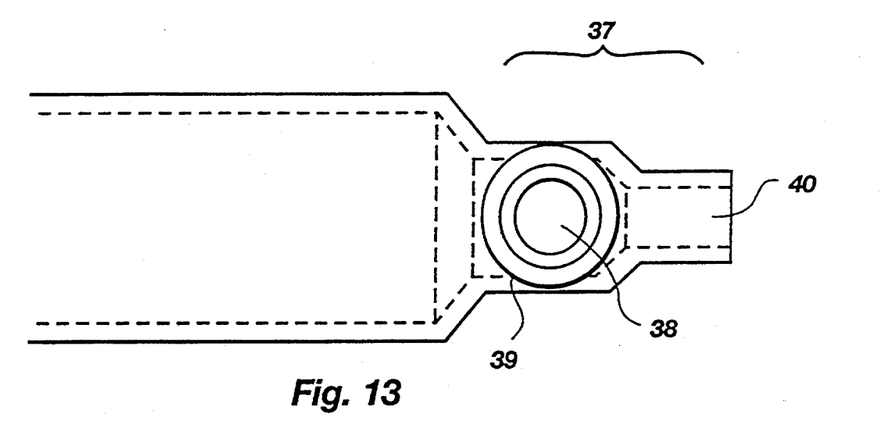
FIG. 13 is a plan view of the discharge nozzle of the syringe of FIG. 1 having an adaptation to accommodate a pressure transducer.
Figure 14:
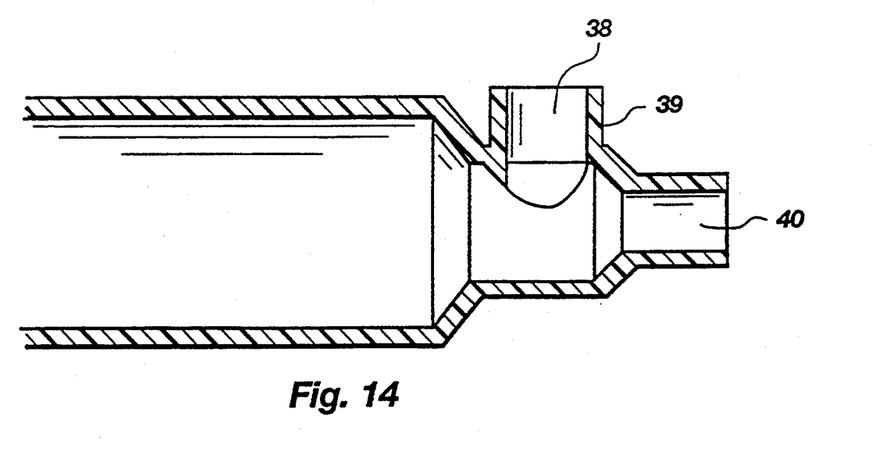
FIG. 14 is an elevational view of the syringe nozzle of FIG. 13.

FIGS. 13 and 14 illustrate another unique feature of the instant invention. The nozzle structure 37 forward of the barrel 11 is modified to be able to hold a pressure transducer (not shown). The pressure transducer fits within receptacle 38 formed by the cylindrical walls 39. The transducer is in contact with fluid inside the nozzle and is capable of accurately determining fluid pressure. Receptacle 38 communicates with flow channel 40 within nozzle structure 37.

In the instant invention, as can be seen in FIG. 1, the syringe body 14 has a barrel supporting portion 13 which, if desired, may contain electronic components suitable for being connected to the transducer for converting the analog electrical output of the transducer to digital outputs. Also, the digital signals may be electronically processed to form infrared information signals capable of being transmitted from the syringe to a remote receiver display, as more fully described in U.S. Pat. No. 5,215,523. The IR transmitting elements, e.g. diodes, may be located on the syringe body and are preferably located at the front of the syringe body on opposite sides of the body so that the wide beam IR signal from each of a pair of IR transmitting elements covers the total region forward, above and below the syringe so that a strong IR information securing signal will be received regardless of the orientation of the syringe.

Plunger, as the term is used herein, refers to the assembly comprising the outer piston, piston rod, any end fittings for the outer piston, any O-rings and the flexible end cap which fits on the distal end of the outer piston.

A dual piston plunger apparatus is described herein which has a modification which limits the extent of reciprocal travel of the inner plunger rod. As illustrated in the above-referenced figures, the extent of travel of the inner plunger rod is limited only by the elasticity of the plunger face (end cap) and the distance the proximal end of the inner piston rod protrudes from the rear of the syringe body. The inner piston rod, in such embodiment, is limited in its travel with reference to the outer piston so that once a particular pressure has been achieved by the plunger, the inner rod then may be reciprocated within a limited longitudinal (axial) travel so that a rather precise change, increase or decrease, in pressure is achieved. As illustrated and discussed hereinafter, other means may be utilized to restrict the distance and/or direction the inner piston travels.

For example, assume that a certain pressure is achieved by advancing the plunger to a certain position within the barrel. Then a reciprocating movement of the inner piston rod may increase the pressure another ten or more percent, depending upon the length of travel, by distending the flexible plunger face (end cap) to cause it to protrude beyond its normal position. By fixing the length of travel of the inner rod, then the change in pressure can be quite accurate, for example, a ten percent increase for a certain predetermined length of travel of the inner piston rod. Thus, a surgeon or medical technician would know exactly how much change in pressure would be achieved by reciprocation of the inner piston rod.

Figure 16:
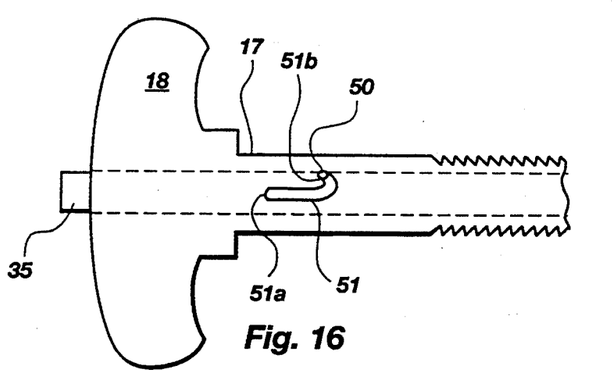
FIG. 16 is an elevational view of an outer piston rod having a "J-shaped" slot penetrating its wall to open into its internal axial bore.

The plunger apparatus with an inner piston rod having a fixed travel is illustrated in one embodiment in FIG. 16. In this embodiment, a pin 50 is attached to the inner piston rod 35 to project laterally and interact with a slot 51 in the wall of the outer piston rod 17. The slot 51 has a fixed longitudinal length. In this embodiment, when the pin rests against the lower rear surface 51a of the slot, the distal end of the inner piston rod is against the internal face of the end cap 29 of the plunger by being slightly extended beyond the distal end of the outer piston (See FIG. 11). Thus, moving the inner piston rod forward distends the face of the flexible end cap to give a precise increase in pressure (See FIG. 12). The operator of this particular angioplasty syringe, upon reciprocating the inner piston rod, would know exactly how much the pressure inside the balloon is being increased even without looking at any pressure gauges or displays.

It is preferred, however, that the distal end of the inner piston 35 (FIG. 17) be co-terminus or slightly extended with respect to the distal end of the outer piston (FIG. 18) when the inner piston is in an inactivated or rest position 51b, i.e. a forward upper position in the slot 51 (FIG. 16). Having a substantially solid surface behind the plunger face (diaphragm) is generally desirable so that the resilient end cap is not under a flexed condition during the axial movement (advancement) of the outer piston. Having the inner and outer piston interlocked, for example, by means of the illustrated pin and slot fixes the inner piston rod to the outer piston rod so that it moves with the outer piston rod during advancement or retraction of the outer piston.

Figures 17, 19, 20, 21:
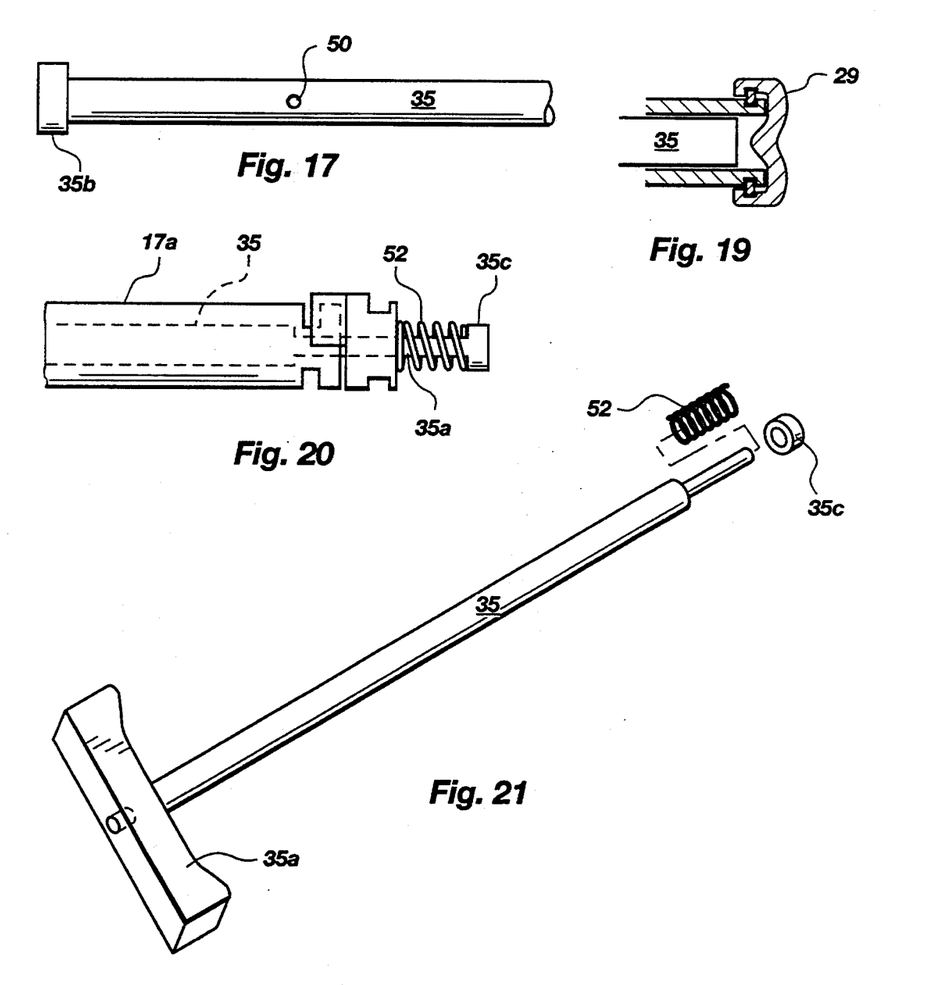
FIG. 17 is an elevational view of an inner piston rod structured to fit inside the axial bore of the outer piston rod of FIG. 16 with a laterally projecting pin member structured to interact with the "J-shaped" slot of the outer piston rod.
FIG. 19 is an elevational, sectional view of the distal end of a plunger having a retracted inner piston rod and a pressure-induced, collapsed flexible end cap.
FIG. 20 is an elevational view of an outer piston distal end assembly having a spring-loaded inner piston.
FIG. 21 is an inner piston rod of the type illustrated in FIG. 20 in which said inner rod has a T-shaped proximal handle.

FIG. 16 illustrates the outer piston 17a of a syringe within a balloon catheter syringe. This outer piston has threads which are engaged by a movable block within the syringe body whereby pressure may be increased in the barrel of the syringe by turning (rotating) the handle of the outer piston rod to force liquid within the syringe barrel forward and through tubing into the balloon catheter to expand the balloon. In this regard, the outer piston rod functions similarly to the piston rods in conventional balloon catheter inflation devices. However, in this embodiment, the outer rod is hollow with a smooth, cylindrical axial bore contained therein which is sized and structured to accept a second piston rod as illustrated in FIG. 17. The second piston rod is preferably longer than the first and projects a short distance from the rear of the handle of the outer piston rod, as illustrated in FIG. 16.

The outer piston rod 17 and the inner rod 35 are structured so that the two are coupled together during advancement or retraction of the outer piston rod. A preferred method for coupling these two rods together is to have a "candy cane" shaped slot 51 in the outer rod, which passes through the wall of the outer rod so that the slot communicates with the smooth, cylindrical, internal bore of the outer rod. The slot, which also may be referred to as a "J"-shaped slot, has the curved portion of the slot closer to the forward or distal portion of the piston rod than toward the proximal end of the piston rod. When the inner piston rod 35 is inserted in the outer piston rod, a hole which has been previously bored transversely in the inner piston rod, is aligned with the slot so that a pin 50 may be inserted through the slot 51 and into the hole in the inner piston rod. The pin 50 is preferably slightly larger in diameter than the hole in the inner piston rod so that by applying force on the pin a secure fit to the inner piston rod is obtained.

The inner piston rod 35 may have a small knob 35b on its proximal end (FIG. 17) so that it may be gripped relatively securely so that it may be rotated easily within the outer piston rod. The engagement of the pin 50 of the inner piston rod with the slot of the outer piston rod is illustrated in FIG. 16, wherein the pin is shown resting in a slight recess 51b in the "head" of the slot. That is, the curved portion of the "J"-shaped slot is curved around to a point of more than 180° with relation to the longitudinal axis of the inner and outer piston rods. Thus, there is a slight recess in which the slot may rest so that it is not easily dislodged.

Figure 18:
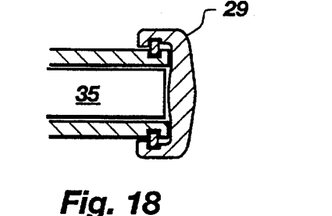
FIG. 18 is an elevational, sectional view of the distal end of a plunger having the distal ends of the inner and outer pistons substantially co-terminus.

When the pin is resting in the recess 51b, then the forward end of the piston rod, that is the distal end of the inner rod, is co-terminus or slightly extended beyond the distal end of the outer piston so that the flexible plunger face (end cap), which seals against the interior of the barrel, and exerts pressure on liquid within the barrel is supported by the distal ends of both piston rods. This is illustrated in FIG. 18.

When the pin has been released from its recess, which is accomplished in the illustrated embodiment by slightly rotating the inner rod very slightly counter-clockwise, pressing it slightly forward in the curved portion of the slot and then rotating the inner piston clockwise (as viewed from the proximal end of the syringe), so that the pin 50 then rests in the straight, elongated portion of the slot, at which time, if there is pressure on the liquid in the syringe barrel, it will press against the flexible end cap 29, and depress it, causing the inner piston rod to move to the rear. This is illustrated in FIG. 19.

By pressing on the proximal end of the inner piston rod projecting from the handle of the outer piston rod with one's thumb, one may press the inner piston rod forward so that the pin reciprocates within the longitudinal portion of the slot of the outer piston rod. By doing this, one can return the inner piston rod 35 to the position shown in FIG. 18, which is to have its face substantially co-terminus or slightly extended in relation to the face of the outer piston rod. Thus, the outer piston rod 17 may be advanced, i.e. by rotation to "screw" it into the syringe barrel, until a predetermined or desired maximum pressure is achieved. By rotating and releasing the inner piston rod and allowing it to regress to the rear position 51a of slot 51 and then reciprocating the inner piston rod 35, the pressure may be fluctuated within the balloon between a maximum desirable, generally predetermined, pressure and a pressure slightly less than that to have a repeated impact (pulsating pressure) by the balloon on plaque within an artery or vessel.

The inner piston rod 35 could be fixed in its relationship to the handle of the outer piston rod by an external attachment (not shown), for example, a bail, similar to the bail on a bucket. Such a bail could be utilized, wherein there is a groove in the rear surface of the knob on the inner piston rod so that the bail would fit in that groove and be positioned with the handle of the outer piston rod such that the inner piston rod would have its distal end substantially co-terminus with the distal end of the outer piston rod when the bail is in position (See FIG. 18). To release the bail, one would press slightly on the inner piston rod knob to advance it slightly, thereby to release the pressure on the bail and the bail could be moved to one side, the inner piston rod allowed to regress, and then the inner piston rod reciprocated similar to the reciprocation achieved in the illustrated embodiments (FIGS. 18 and 19).

The advantage of the pin and slot mechanism illustrated herein is that the length of reciprocation is fixed by the length of the slot. There is no danger of the piston rod falling out of the internal bore of the outer rod nor any possibility that the inner piston rod can be advanced farther forward than desired. The forward advancement of the inner piston rod, of course, could be determined by placement of the knob 35b on the inner piston rod so that the farthest forward position of the inner piston rod would be determined when the knob on its proximal end was in contact with the rear surface of the handle 18 on the outer piston rod.

The illustrated embodiment for controlling the traverse travel of the inner piston rod with relation to the outer piston rod can have applicability to dual piston rod arrangements other than those which have a single end cap (plunger face) across the distal ends of both piston rods. The mechanism of locking the two piston rods together could be useful in any arrangement wherein an outer and inner piston rod is utilized.

Thus, the instant invention may be utilized to pressurize balloon catheter to a certain maximum pressure, then relieve the pressure a certain predetermined amount, and then rapidly return the pressure to the maximum amount and to the lower amount repeatedly.

Another embodiment particularly useful for the purposes of the instant invention is illustrated in FIG. 20 wherein the inner piston rod is spring loaded to hold it in a forward position against the interior surface of the flexible plunger face (end cap) to prevent the plunger face from being substantially collapsed when the plunger mechanism is advanced to pressurize fluid within the syringe barrel.

In FIG. 20, the spring 52 is a coil spring fitted concentrically around the distal shaft portion of the inner piston rod 35. In this embodiment the distal end of the inner rod has a retaining cap 35c securely fitted to the distal end of the inner rod. A T-shaped handle 35a is attached to the proximate end of the inner piston rod (See FIG. 21).

Figure 22:
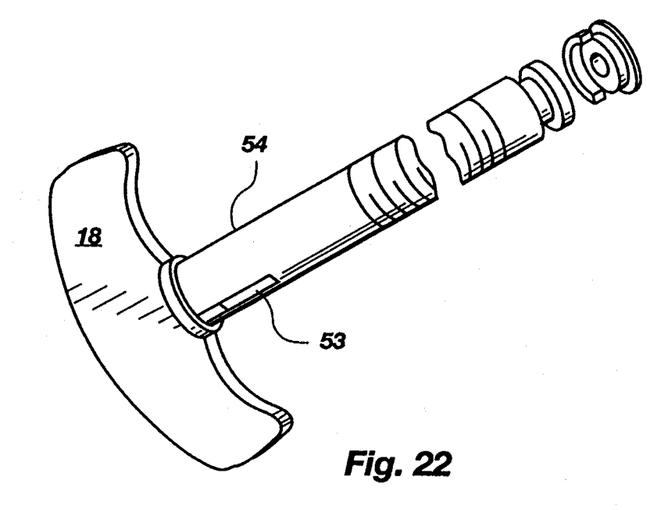
FIG. 22 is an outer piston rod having opposed lateral slots in its sidewall to accommodate the T-shaped proximal handle of the inner piston rod illustrated in FIG. 21.

The outer piston rod 17a has a pair of slots 53 and 54 (see FIG. 22) opposed to each other to accommodate the T-shaped handle 35a of the inner piston rod. The lengths of the slots 53 and 54 are sufficient to allow longitudinal movement of the T-shaped handle of the inner rod. An operator of the syringe can, with one hand, grip both the handle 18 of the plunger and the inner rod handle 35a and, by squeezing, move the handle of the inner rod to the rear, i.e. towards the plunger handle, to move the inner rod rearward, thus moving the distal retaining cap 35c of the inner rod to the rear to allow the flexible plunger face to collapse, thus reducing the pressure of liquid in the syringe barrel. Then, by releasing the inner rod handle, the compressed spring rebounds to return the plunger face (end cap 29; see FIG. 18) to its original shape to return the barrel pressure to its original pressure.

This particular embodiment is very desirable inasmuch as there is no chance of exceeding the maximum pressure attained when the plunger is initially advanced to its forward position, i.e. that position which gives the predetermined maximum desired pressure. Relaxation of the flexible face of the plunger diminishes the pressure a small but significant amount, e.g. 10% or more.

Repeated squeezing of the inner rod handle causes a pulsating pressure within the balloon, which is very effective for compacting plaque within a vessel, without exceeding the desired preselected maximum pressure.

Even if the pressure on the plunger face causes some slight compression of the spring when the plunger is advanced to its forward position, further compression of the spring followed by its release will not return the spring beyond its slightly compressed state and thus not exceed the maximum pressure previously attained.

Alternatively, the spring may be located at the proximal end of the syringe wherein a compression-type spring is contained within the plunger handle and contacts the T-shaped handle of the inner rod to maintain the distal end of the inner rod against the inner surface of the flexible face of the plunger end cap.

Figure 23:
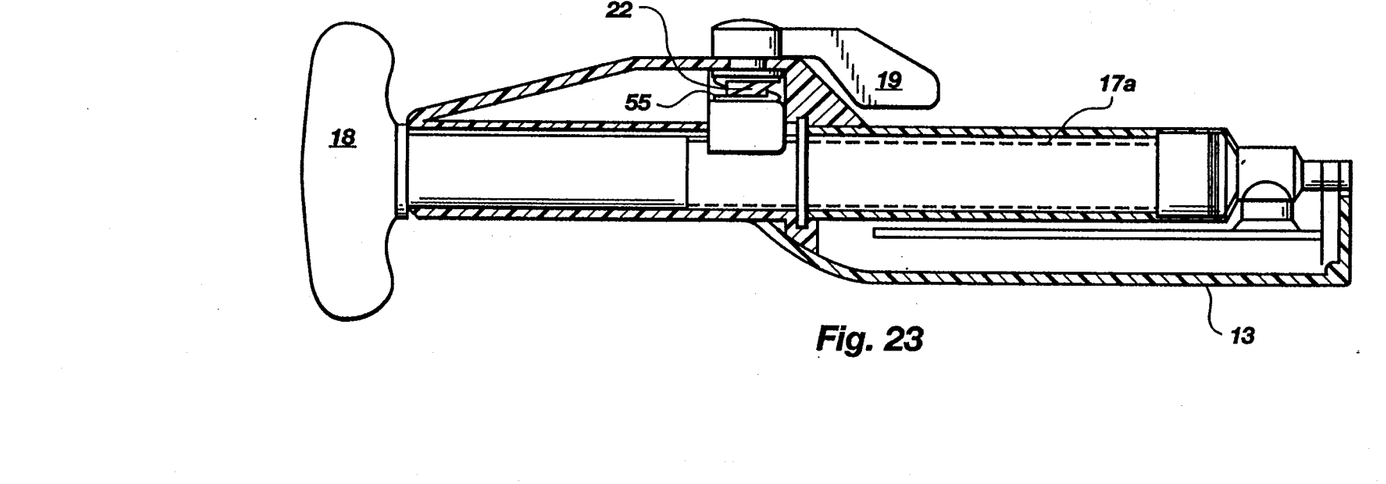
FIG. 23 is an elevational, sectional view of a balloon catheter syringe having a spring-loaded plunger release mechanism.

The plunger release mechanism illustrated in FIGS. 2 and 3 can be spring actuated as illustrated in FIG. 23. The spiral spring forces the splined block 20 against the threaded portion 17a (See FIG. 5) of the piston rod 17. The top of the spiral spring 55 rests against the interior shell of the body to force the splined block downward. Rotation of the wing-type handle 19 rotates the cam race 22 which engages a protrusion within threaded block 20, in effect, "screws" the cam race 22 into the threaded block to raise it. Release of the wing-like handle allows the spring to force the splined block downward against the threads of the piston rod, which returns the handle 19 to the "engagement" position. The orientation of the spring, the spiral-type spring, and the ease of moving the wing-like handle 19 make the structure of the instant syringe particularly useful. The syringe may be easily gripped in the palm of the hand and the wing-like handle easily moved by the thumb of the hand holding the device.

A preferred spiral spring is one known in the art as a crest-to-crest wave spring wherein the spring completes a single 360° circle between its free end.

Although other devices use spring-loaded blocks, the type of spring, the orientation of a spiral-like spring and the structure and function of the release/engagement mechanism of the instant invention are unique.

What is claimed is:

1. A balloon catheter syringe having a syringe body comprising:
   a barrel with an inner bore of substantially uniform diameter supported by said syringe body;
   a resilient plunger end cap member sized to make sealing contact with said inner bore of said barrel, said plunger having a continuous face for contacting a fluid within said barrel and a backside structured to engage the distal end of a piston;
   an outer piston reciprocally moveable within said inner bore of said barrel, said outer piston joined to said end cap, said outer piston being joined at one end to a proximal handle and having an internal bore structured to receive a second, smaller piston;
   a second piston slidingly engaging said internal bore of said outer piston, said second piston having a distal end structured to engage the backside of said resilient plunger end cap member and capable of causing said end cap member face to flex when said inner piston is moved against or removed from contacting the backside of said end cap member; and
   means for restraining length of travel of said inner piston within said outer piston.

2. The balloon catheter syringe of claim 1, wherein said restraining means comprises a predetermined proximal length of second piston extending from the rear of the handle of the outer piston when said second piston has its distal end in substantial contact with the backside of said end cap.

3. The balloon catheter syringe of claim 1, wherein said restraining means comprises a lateral projection on said second piston which engages a slot opening having a straight portion of a predetermined length in the wall of said outer piston, said lateral projection being restrained in the distance it can reciprocate lengthwise by said slot.

4. The balloon catheter syringe of claim 1, wherein said restraining means is structured to position said second piston in its rest position so that it is in a forward position such that its distal end is in substantial contact with the backside of said resilient end cap.

5. The balloon catheter syringe of claim 3, wherein said slot is a "J" shaped slot having the curved portion of the "J" in a forward location.

6. The balloon catheter syringe of claim 5, wherein the lateral projection resides at the end of the curved portion of the "J" shaped slot when the second piston is in a rest position.

7. The balloon catheter syringe of claim 1, wherein said means for restraining length of travel of said inner piston is a spring member interacting with said second piston which causes the distal end of said second piston to contact the backside of said end cap and which resists pressure on the face of said end cap to prevent any substantial rearward movement of said second piston.

8. The balloon catheter syringe of claim 7 wherein said second piston is structured to have retraction means whereby a force can be externally applied to said second piston to retract said piston to allow the resilient end cap face to collapse from pressure existing in the barrel of the syringe.

9. The balloon catheter of claim 8 wherein said retraction means is a handle positioned near the proximal end of said piston, said handle being positioned forward of said outer piston handle whereby said second piston handle may be moved rearward by squeezing both handles with one hand.

10. A balloon catheter syringe having a syringe body and a barrel having a plunger tightly fitting within said barrel, a threaded plunger rod fitted to said plunger and a moveable thread engaging member interacting with said threaded plunger; the improvement comprising:
    a cylindrical cam member rotatably attached to said syringe body rotatable about its longitudinal axis having means to interact with said thread engaging member to engage and disengage said thread engaging member from the threads of said threaded plunger rod upon rotation of said cam member in opposite directions whereby said thread engaging member moves towards or away from said threaded plunger rod upon rotation of said cam member in different directions,
    a compression spring member structured to interact with said thread engaging member to maintain said thread engaging member in an engaged position.

11. A balloon catheter syringe having a barrel, a displaceable piston and a threaded piston rod attached at its distal end to said displaceable piston, said syringe comprising:
    a syringe body for supporting said barrel;

a smooth bore contained within said body, said bore size to receive said piston;

a splined block contained within said syringe body, said block displaceable transversely to said piston rod to occupy two positions, a first position being a piston rod thread engaging position and a second disengaging position;

a splined block actuator mechanism having a threaded screw member rotatably attached to said body with the threaded position of said screw engaging said splined block whereupon rotation of said screw around its central longitudinal axis in one direction causes said splined block to engage said piston rod and rotation of said screw in an opposite direction disengages said splined block from the threads of said piston rod; and a spiral compression spring structured to encircle said screw member and supported at one end by the syringe body and at the other end said spring contacting said splined block to maintain said block in an engaged position.

12. The balloon catheter syringe of claim 11 wherein said spiral spring is structured to complete substantially only one revolution around said screw member.

* * * * *

UNITED STATES PATENT AND TRADEMARK OFFICE
CERTIFICATE OF CORRECTION

PATENT NO. : 5,433,707
DATED : 7/18/95
INVENTOR(S) : Evan Call

It is certified that error appears in the above-indentified patent and that said Letters Patent is hereby corrected as shown below:

In Column 4, line 40, insert a comma after "position" (first occurrence); and

In Column 13, line 2, change "size" to --sized--.

Signed and Sealed this

Nineteenth Day of December, 1995

Attest:

BRUCE LEHMAN

Attesting Officer     Commissioner of Patents and Trademarks